United States Patent [19]

Clausen et al.

[11] Patent Number: 4,997,451
[45] Date of Patent: Mar. 5, 1991

[54] OXIDATIVE HAIR DYEING COMPOSITIONS BASED ON 4-AMINOPHENOL DERIVATIVES AND NEW 4-AMINOPHENOL DERIVATIVES

[75] Inventors: Thomas Clausen; Wolfgang Balzer, both of Alsbach; Anke Flohr, Frankfurt, all of Fed. Rep. of Germany

[73] Assignee: Wella Aktiengesellschaft, Darmstadt, Fed. Rep. of Germany

[21] Appl. No.: 497,397

[22] Filed: Mar. 22, 1990

[30] Foreign Application Priority Data

Apr. 29, 1989 [DE] Fed. Rep. of Germany ....... 3914253

[51] Int. Cl.$^5$ ............................................. A61K 7/13
[52] U.S. Cl. ......................................... 8/421; 8/407; 8/408; 8/412; 564/443
[58] Field of Search .................. 8/421, 412, 408, 407; 564/443

[56] References Cited

FOREIGN PATENT DOCUMENTS 3441148 5/1986 Fed. Rep. of Germany
3538750 5/1987 Fed. Rep. of Germany Primary Examiner—A. Lionel Clingman
Assistant Examiner—William S. Parks
Attorney, Agent, or Firm—Michael J. Striker

[57] ABSTRACT

Compositions for oxidative dyeing of hair based on 4-aminophenol derivatives of the formula (I):

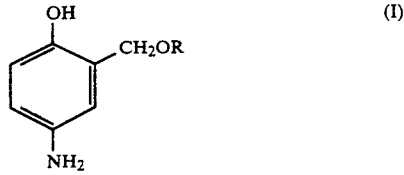

or their physiologically compatible water soluble salts, wherein R is selected from the group consisting of alkyl groups with from one to four carbon atoms, monohydroxyalkyl groups with from two to four carbon atoms, aminoalkyl groups with from two to four carbon atoms, aminoalkyl groups having amino groups substituted with from one to two alkyl groups having from one to four carbon atoms and dihydroxyalkyl groups with from three to four carbon atoms. New developer substances include 4-amino-2-propoxymethyl phenol, 4-amino-2-isopropoxymethyl phenol and 4-amino-2-(2'-hydroxyethoxymethyl)-phenol. The developer substances of the formula I have physiologically improved properties with equally good dyeing properties as the p-aminophenol used up to now in the red region of the spectrum.

16 Claims, No Drawings

OXIDATIVE HAIR DYEING COMPOSITIONS BASED ON 4-AMINOPHENOL DERIVATIVES AND NEW 4-AMINOPHENOL DERIVATIVES

BACKGROUND OF THE INVENTION

Our invention relates to oxidative hair dyeing compositions based on 4-aminophenol derivatives as a developer substance and new 4-aminophenol derivatives.

Oxidative hair dyes have considerable importance in the art of dyeing hair. The dyes are made by coupling of developer substances and coupler substances in the hair dyeing art. This leads to very intense hair colors with very good color depth. Moreover different color shades are made by combination of different developer and coupler substances.

The compounds 2,5-diaminotoluene, 2,5-diaminobenzyl alcohol, 2,5-diaminophenylethyl alcohol, p-aminophenol and 1,4-diaminobenzene especially are used as developer substances. Resorcinol, 4-chlororesorcinol, 1-naphthol, m-aminophenol and derivatives of the m-phenyldiamines are used as coupler substances.

Oxidative hair dyes which are used to color human hair have numerous special requirements. Thus they must be unobjectionable in regard to toxicological and dermatological considerations and must produce sufficiently intense color shades. The hair dye on the hair is required to have good light fastness, permanent wave fastness, acid fastness and fastness to rubbing or abrasion.

In every case however such a hair dye must remain stable for at least 4 to 6 weeks despite the action of light, friction and chemical means. Moreover it is required that a wide range of different color shades can be made by combination of suitable developer and coupler components.

p-Aminophenol, alone or in a mixture with other developer substances, in combination with suitable coupler substances is especially preferred for producing natural and especially fashionable shades.

Considerations regarding physiological compatibility are currently being raised against the p-Aminophenol developer substances for the red part of the color spectrum, while more recently the developer substances recommended, e.g. pyrimidine derivatives, cannot be completely satisfactory in regard to dyeing.

Much research and development has been aimed at elimination of the disadvantage of poor physiological compatibility of the p-aminophenol developer substances used in the red region.

Thus oxidative hair dyeing compositions with a content of 4-amino-2-hydroxymethylphenol, which lead only to satisfactory hair color in the red range with a slight improvement relative to p-Aminophenol, are known and described in German Published Patent Applications DE-OS 3 441 148 and DE-OS 3 538 750.

SUMMARY OF THE INVENTION

It is an object of the present invention to provide an oxidative hair dyeing composition based on developer substances for the red range, which is comparable in color intensity and brightness with p-Aminophenol but has improved physiological compatibility.

Accordingly the oxidative hair dyeing composition of our present invention contains at least one developer substance and at least one coupler substance, said developer substance being a 4-aminophenol derivative of the following general formula (I),

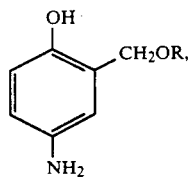

or a physiologically compatible water soluble salt thereof, wherein R is a substituted alkyl group with 1 to 4 carbon atoms, a monohydroxyalkyl group with 2 to 4 carbon atoms, an aminoalkyl group with from two to four carbon atoms, an aminoalkyl group with from two to four carbon atoms, in which the amino groups are substituted with from one to two alkyl groups having 1 to 4 carbon atoms or a dihydroxyalkyl group with from three to four carbon atoms. These compounds attain the object of our invention in an outstanding way.

The water soluble salts of the compounds of the general formula I are obtained by reaction with suitable organic and inorganic acids and bases.

The chloride, sulfate, phosphate, acetate, lactate and citrate salts are suitable as the physiologically compatible, water soluble salts of the invention. The compounds of the general formula I are sufficiently water soluble and have an outstanding chemical stability, especially as components in the hair dyeing compositions according to our invention.

The developer substances according to the invention, of which the 4-amino-2-methoxymethylphenol and 4-amino-2-ethoxymethylphenol and the new compounds 4-amino-2-propoxymethylphenol, 4-amino-2-isopropoxymethylphenol and 4-amino-2-(2'-hydroxyethoxymethyl)-phenol are preferred, should be present in general in an amount of about 0.01 to 3.0 percent by weight, advantageously 0.1 to 2.5 percent.

Although the advantageous properties of the new developer substances described here are obviously superior to the currently used developers, it is understandable also that the new developer substances of formula I can be used with known developer substances such as e.g. 1,4-diaminobenzene, 2,5-diaminotoluene, or 2,5-diaminobenzyl alcohol.

The following components are suitable as coupler substances in hair dyeing compositions and are currently known: 1-naphthol, resorcinol, 4-chlororesorcinol, 4,6-dichlororesorcinol, 2-methylresorcinol, 2-amino-4-(2'hydroxyethylamino)-anisol, 2,4-diaminobenzyl alcohol, m-phenylenediamine, 5-amino-2-methylphenol, 2,4-diaminophenoxyethanol, m-aminophenol, 3-amino-4-chloro-6-methylphenol, 3-amino-2-methylphenol, 4-amino-2-hydroxyphenoxyethanol, 4-hydroxy-1,2-methylenedioxybenzene, 4-(2'-hydroxyethylamino)-1,2-methylenedioxybenzene, 2,4-diamino-5-ethoxytoluene, 4-hydroxyindole, 3-amino-5-hydroxy-2,6-dimethoxypyridine and 3,5-diamino-2,6-dimethoxypyridine.

The individual coupler substances are contained in the hair dyeing composition advantageously in an amount of from about 0.01 to 3 percent by weight, preferably of from 0.1 to 2.5 percent by weight.

The coupler and developer substances can be contained in the hair dyeing composition individually or mixed with each other.

The total amount of developer and coupler substances contained in the hair dyeing compositions amounts to from about 0.1 to 6.0 percent by weight, advantageously 0.5 to 4.0 percent by weight.

Additionally the hair dyeing compositions of this application can have additional dyeing components, e.g. with self-coupling preliminary dyeing substances, such as 6-amino-2-methylphenol and 2-amino-5-methylphenol and other common direct dyeing substances such as for example Triphenylmethane dye and Diamond Fuchsin(C.I. 42 510) and Leather Ruby HF (C.I. 42520), aromatic Nitrodyes such as 2-nitro-1,4-diaminobenzene, 2-amino-4-nitrophenol, 2-amino-5-nitrophenol, 2-amino-4,6-dinitrophenol, 2-amino-5-(2'-hydroxyethylamino)-nitrobenzene and 4-(2'-hydroxyethylamino)-3-nitrotoluene, 1-[(2'-Ureidoethyl)-amino]-4-nitrobenzene and azodyes, such as Acid Brown 4 (C.I. 14 805) and Dispersive dye stuffs, such as for example 1,4-diaminoanthraquinone and 1,4,5,8-Tetraaminoanthraquinone.

Additional suitable dyes absorbed directly on hair are for example described in the reference book, J.C.Johnson "Hair Dyes", Noyes Data Corp., Park Ridge, USA (1973), Pages 3 to 91 and 113 to 139(ISBV:0-8155-0477-2).

Understandably the coupler and developer substances and other hair dyeing components in so far as they are basic substances may also be added in the form of their physiologically compatible acid addition salts, especially the hydrochloride or sulfate or further—in case they have aromatic OH groups—in the form of salts with bases, e.g. alkali phenolates.

Moreover still further common cosmetic additives, e.g. antioxidants such as ascorbic acid, thioglycolic acid or sodium sulfite and perfumes, complex formers, wetting agents, emulsifiers, thickeners and hair care agents can be used.

The preparations can be in the form of a solution, especially an aqueous or aqueous-alcoholic solution. Especially preferred preparations include however a cream, a gel or an emulsion. The new hair dyeing compositions are produced by mixing hair dyeing components with the common additives for such preparations.

Solvents are common additives in solutions, creams, emulsion or gels. These common solvents include water, lower aliphatic alcohols, e.g. ethanol, propanol and isopropanol, or glycols such as 1,2-propyleneglycol, and glycerin, additional wetting agents or anionic, cationic or amphoteric emulsifiers or nonionogenic surface active substances, such as fatty alcohol sulfates, ethoxylated fatty alcohol sulfates, alkyl sulfates, alkyl benzene sulfonates, alkyltrimethylammonium salt, alkyl betain, ethoxylated fatty alcohols, ethoxylated nonyl phenols, fatty acid alkanolamides, ethoxylated fatty acid esters, additional thickeners such as higher fatty alcohols, starch or cellulose derivatives, Vaseline, paraffin oil and fatty acids and moreover hair care agents such as cationic resins, lanolin derivatives, cholesterol, Pantothenic acids and Betain. The mentioned components are used in the usual amount, for example the wetting and emulsifiers are used in a concentration of about 0.5 to 30 percent by weight, the thickeners in about 0.1 to 25 percent by weight and the hair care agents in a concentration of about 0.1 to 5.0 percent by weight.

According to their composition the hair dyeing compositions of the present invention can be weakly acid, neutral or alkaline. Particularly the pH can be in the range between 8.0 and 11.5. The pH of the compositions of the invention can be adjusted with ammonia. Also organic amines, e.g. monoethanolamines and triethanolamines or other inorganic bases such as sodium hydroxide and potassium hydroxide can be used.

For oxidative dyeing of hair using the compositions of our invention one mixes the previously described hair dyeing compositions directly prior to use with an oxidizing agent and applies an amount sufficient for hair treatment, usually from about 60 to 200 g, to the hair according to the feel of the hair.

As an oxidizing agent for development of hair color hydrogen peroxide or its addition compounds to urea, melamine or sodium borate in the form of a 3 to 12 percent aqueous solution, advantageously 6%. If a 6% aqueous hydrogen peroxide solution is used as oxidizing agent, the weight ratio of hair dyeing composition to oxidizing agent amounts to 5:1 to 1:2, advantageously however 1:1. Larger amounts of oxidizing agent are used particularly with higher dye concentrations in the hair dyeing composition or if simultaneously a stronger bleaching of the hair is to be avoided. One allows the mixture to act on the hair about 10 to 45 minutes, advantageously 30 minutes at 15 to 50° C. then the hair is rinsed with water and dried. If necessary it is washed with Shampoo in connected with the rinsing and, as the case requires, with a weak organic acid, for example citric acid or tartaric acid. Subsequently the hair is dried.

The 4-aminophenol derivatives of the above general formula (I) are partially known. Thus e.g. a process for making the 4-amino-2-methoxymethylphenol and the 4-amino-2-ethoxymethylphenol is described in the German Patent 148 977.

The 2-hydroxy-5-nitrobenzyl chloride is useful as a starting material. It is reacted with methanol and/or with ethanol and sodium carbonate to obtain the ethyl ether of 2-hydroxy-5-nitrobenzyl alcohol, which is subsequently reduced with zinc dust in aqueous alcoholic solution to the corresponding 4-aminophenol derivatives. The possibilities for this synthetic path are limited considerably of course by the sensitivity of the starting material and by its toxicological properties.

The 4-aminophenols of the general formula I may also all be be satisfactorily made in larger quantities according to the following reaction scheme:

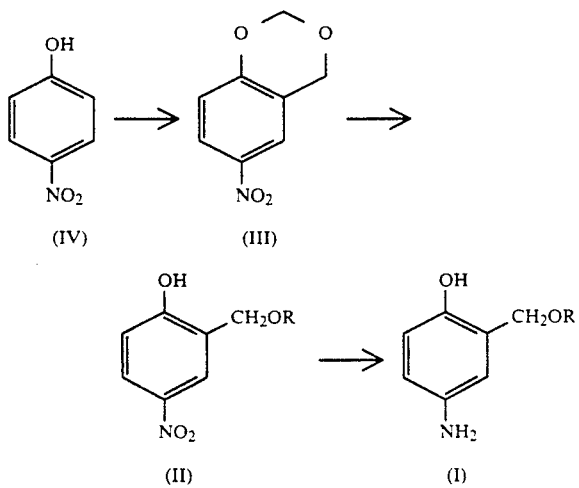

The starting material for the above synthesis is 4-Nitrophenol which is available industrially. One obtains compound III when 4-nitrophenol is acted on by formalin and sulfuric acid (W. Borsche and A.D. Berghout, Ann. 330, 82(1904). Subsequently a ring opening occurs by conversion with the corresponding alcohol and sulfuric acid to form the benzylether II in which R has the same significance as that indicated for formula I(according to I.Stavropvskaya, Z.Obsc.Chim. 24,2068(1954)). Catalytic hydrogenation of the nitro group provides the 4-aminophenol derivative of the general formula I in good yield.

The process for making of the compound of formula I is described in greater detail in Example 1. The preparation of the common compounds of formula I occur in a way that is analogous to this process.

The developer substances of formula I should be used in hair dyeing compositions either as the free base or in the form of a physiologically compatible water soluble salt with suitable inorganic or organic acids, e.g. as the chloride, sulfate, phosphate, acetate, propionate, lactate or citrate. The compounds of formula I are sufficiently soluble in water, they also have an outstanding stability, especially as components of the hair dyeing compositions described here.

The hair dyeing composition according to the invention based on 4-aminophenol derivatives of the general formula I as developer substances permit hair dyeing with outstanding fastness properties, especially relating to light fastness, washability and fastness to rubbing and friction, which may be stripped again with reducing agents.

The progress made by the use of the substituted 4-aminophenols in the hair dyeing compositions described in this application in regard to toxicological and dermatological properties is of particular significance in comparison to the developer substances which are already know such as 4-aminophenol and 4-amino-2-hydroxymethylphenol.

Thus the compound 4-amino-2-hydroxymethylphenol is mutagenic according the Ames mutagenicity test, while the 4-amino-2-methoxymethylphenol according to the invention is not mutagenic.

A wide range of possible color shades is offered by the hair dyeing compositions of the invention according to the kind and amount of the the various dye components. These colors include blonds, browns, purples, violettes, blues and blacks. These color shades are characterized by their particularly good color intensities and stabilities.

This is particularly clear in comparing hair dyeing compositions, which contain as developer substances on the one hand the known developer substances p-aminophenol, 4-amino-2-methylphenol, 4-amino-2-hyroxymethylphenol or 4-amino-3-methylphenol and on the other hand the developer substances of the present invention.

During the 4-amino-2-methylphenol and 4-amino-2-hydroxymethylphenol provide comparatively weaker and bluer shades than the standard p-aminophenol, the use of the substituted 4-aminophenol derivative of the general formula I leads surprisingly to approximately the same color shades as with a comparable color depth. The 4-amino-3-methylphenol, which is a structurally similar compound, results in a considerably reduced color depth than the 4-aminophenol derivatives of the present invention.

The exceptionally good dyeing properties of the hair dyeing compositions according to the present invention are illustrated by their coloring of gray, chemically undamage hair without problems and with good coverage.

The following examples serve to illustrate the invention in greater detail.

EXAMPLES

Preparation of Substituted 4-Aminophenol Derivatives

EXAMPLE 1

Process for making the substituted 4-aminophenol of the general formula I

Step 1: Preparation of 6-Nitro-1,3-benzodioxan III 10.8 g(0.08 Mol) of 4-Nitrophenol are dissolved in 12 ml of 40% formalin with heating and mixed with a mixture of 6 ml of water and 24 ml of concentrated sulfuric acid. A solid mass arises with stirring, which is mixed with 200 ml of water after one hour and filtered with suction. The precipitate is recrystallized from ethanol. After drying one obtains 8.5 g (60 percent theoretical) of light brown crystals with a melting point of from 146° to 148° C.

Step 2: Production of 2-hydroxy-5-nitrobenzyl ether of formula II 30 g(0.17 Mol) 6-Nitro-1,3-benzodioxan III are dissolved in 300 ml of certain alcohols. After addition of 15 ml of water 60 ml concentrated sulfuric acid is added dropwise with stirring. The solution is heated under reflux until completely converted to product with the help of a control by thin layer chromatography. After cooling the reaction mixture is mixed with about 200 ml water and the solution is concentrated to about ⅓ of its volume under vacuum. A yellow oil comes down which is extracted with ether. The ether phase is dried by sodium sulfate and the residue is filtered by silica gel with methylene chloride as elution agent. After concentration of the methylene chloride solution light yellow crystals of the corresponding 4-nitrophenol compound precipitate.

| 4-Nitrophenol Derivatives of the General Formula II: | | |
|---|---|---|
| R | Reaction Time, hrs | Yield, % theoretical | Melting Point, °C. |
| —CH$_3$ | 8 | 71 | 106 |
| —C$_2$H$_5$ | 2.5 | 65 | 82 |
| -n-C$_3$H$_7$ | 3 | 77 | 50 |
| -iso-C$_3$H$_7$ | 2.5 | 55 | 67 |
| —C$_2$H$_4$OH | 3 | 80 | 138 |

Step 3: Reduction of the Nitrophenol of formula II

The nitrocompounds of the general formula II are hydrogenated in methanol or ethanol using palladium-/activated charcoal catalyst(5%) with hydrogen at ambient temperature until they are completely saturated. After filtration with suction of the catalyzed solution and concentration of the solution the 4-aminophenols of the general formula I precipitate. If necessary they are recrystallized from acetone. By addition of methanolic HCl solution to the raw starting filtrate and subsequent concentration of that solution the hydrochloride of the 4-aminophenol derivatives of the invention is obtained.

New 4-aminophenol derivatives of the general formula I

Ia: 4-amino-2-propoxymethyl phenol hydrochloride, gray crystals with a melting point of 260° C. (with decomposition)

¹H-NMR(DMSO-d₆): δ=0.91(t, J=7.4 Hz, 3 H, —CH₂—CH₂—CH₃); 1.58(m, 2H, —CH₂—CH₂—CH₃); 3.44 (t, J=6.5 Hz, 2H, —CH₂—CH₂—CH₃); 4.42 (s, 2 H, —CH₂—O—); 6.93 (d, J=8.4 Hz, 1 H, Aromatic-H); 7.13 (dd, J=8.4 Hz and 2.2 Hz, 1 H, aromatic-H); 7.28 (d, J=2.2 Hz, 1 H, Aromatic-H); 10.17 (s, 3 H, —OH and —NH₂, exchange with D₂O).

Ib: 4-amino-2-isopropoxymethylphenol hydrochloride, gray crystals with a melting point of 280° C. (with decomposition)

¹H-NMR (DMSO-d₆): δ=1.15 (d, J=5Hz, 6H, —CH(CH₃)₂); 3.67 (m, 1H, —CH(CH₃)₂); 4.43 (s, 2H, —CH₂—O); 6.93 (d, J=8.5 Hz, 1 H, aromatic-H); 7.13(dd, J=8.5 Hz and 2.6 Hz, 1 H, aromatic-H); 7.28 (d, J=2.6 Hz, 1 H, aromatic-H); 10.01(s, 1H, —OH, exchange with D₂O); 10.19 (s, H, —NH₂, exchange with D₂O).

Ic: 4-amino-2-(2'-hydroxyethoxymethyl)-phenol hydrochloride, brown oil ¹H-NMR (DMSO-d₆): δ=3.17 (s, 2H,—O—CH₂—CH₂—OH); 3.39 (s, 2H, —O—CH₂—CH₂OH); 4.25 (s, 3H, —OH, exchange with D₂O); 4.47 (s, 2H, —CH₂—O—), 6.94(d, J=8.5 Hz, 1 H, aromatic-H); 7.15(dd, J=8.5 Hz and 2 5 Hz, 1 H, aromatic-H); 7.38(d, J=2.5 Hz, 1 H, aromatic-H); 10.16 (s, 2H, —NH₂, exchange in D₂O).

HAIR DYEING COMPOSITION EXAMPLES

EXAMPLE 2

Hair Dyeing Composition in Gel Form

```
0.59 g   4-amino-2-ethoxymethyl phenol hydrochloride
1.00 g   2-amino-4-(2'-hydroxyethyl)amino anisole sulfate
0.15 g   sodium sulfite, water free
5.00 g   lauryl alcohol diglycol ether sulfate-sodium salt
         (25%, aqueous solution)
1.00 g   hydroxyethyl cellulose, highly viscous
10.00 g  ammonia, 22% aqueous solution
82.26 g  water
100. g
```

50 g of the above-mentioned hair dye composition are mixed shortly prior to use with 50 g hydrogen peroxide solution (6%) and the mixture is subsequently applied to blond natural hair. After an acting time of 30 minutes at 40° C. the hair is rinsed with water and dried. The hair has an intense red color.

EXAMPLE 3

Hair Dyeing Composition in Gel Form

```
0.35 g   4-amino-2-methoxymethyl phenol
0.27 g   5-amino-2-methylphenol
0.30 g   ascorbic acid
15.00 g  oleic acid
7.00 g   isopropanol
10.00 g  ammonia, 22% aqueous solution
67.08 g  water
100. g
```

Just prior to use one mixes 50 g of this hair dyeing composition with 50 g of hydrogen peroxide solution (6 percent) and allows the mixture to act for 30 minutes on white human hair at 40° C. Then the hair is rinsed with water and dried. The hair is colored with an orange shade.

EXAMPLE 4

Hair Dyeing Composition in Cream Form

```
1.30 g   4-amino-2-isopropoxymethylphenol hydrochloride
1.10 g   1-Naphthol
15.00 g  Cetyl alcohol
0.30 g   sodium sulfite, water free
3.50 g   lauryl alcohol diglycol ether sulfate-sodium salt
         (28% aqueous solution)
3.00 g   ammonia, 22% aqueous solution
75.80 g  water
100. g
```

50 g of these hair dyeing compositions are mixed with 50 grams of hydrogen peroxide solution shortly prior to use. Subsequently one applies the mixture on natural blond hair and allows it to act for 30 minutes at 40° C. After that the hair is rinsed with water and dried. The hair has attained an intense red color.

EXAMPLE 5

Hair Dyeing Solution

```
0.80 g   4-amino-2-methoxymethyl phenol
0.12 g   resorcinol
0.10 g   m-aminophenol
0.50 g   5-amino-2-methylphenol
0.15 g   2-amino-4-(2'-hydroxyethyl)-amino anisole sulfate
0.05 g   1-naphthol
10.00 g  lauryl alcohol diglycol ether sulfate sodium salt,
         (28%, aqueous solution)
78.28 g  water
100. g
```

Shortly prior to use one mixed 50 g of the above described hair dyeing composition with 50 g of hydrogen peroxide solution (6%) and allows the mixture to act for 30 minutes on natural blond hair at 40° C. Then the hair is rinsed with water and dried. The hair is dyed in fashionable, golden color shades.

EXAMPLE 6

Hair Dye Composition in Gel Form

```
0.90 g   4-amino-2-ethoxymethyl phenol hydrochloride
0.80 g   2,5-diaminotoluene sulfate
0.22 g   2-amino-4-(2'-hydroxyethyl)-amino anisole sulfate
0.20 g   5-amino-2-methylphenol
0.02 g   1-[(2'-Ureidoethyl)-amino]-4-nitrobenzene
0.05 g   2-nitro-p-phenylenediamine
0.15 g   sodium sulfite, water free
2.50 g   lauryl alcohol diglycol ether sulfate sodium salt
         (28%, aqueous solution)
0.80 g   hydroxycellulose, highly viscous
6.00 g   ammonia, 22% aqueous solution
88.36 g  water
100. g
```

50 g of the above-mentioned hair dyeing composition are mixed with 50 g of hydrogen peroxide solution (6%) prior to use and the mixture is applied subsequently to natural blond hair. After a reaction time of 30 minutes at 40° C. the hair is rinsed with water and dried. The hair has obtained a fashionable copper-brown color.

Unless otherwise mentioned % in this application indicates weight percentages.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Composition for oxidative dyeing of hair containing at least one developer substance and at least one coupler substance, wherein said developer substance comprises a 4-aminophenol derivative of the formula (I):

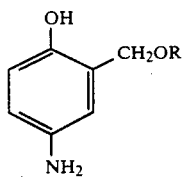

or a physiologically compatible water soluble salt thereof, wherein R is selected from the group consisting of alkyl groups with from one to four carbon atoms, monohydroxyalkyl groups with from two to four carbon atoms, aminoalkyl groups with from two to four carbon atoms, aminoalkyl groups having amino groups with from two to four carbon atoms in which said amino groups are substituted with from one to two alkyl groups having one to four carbon atoms and dihydroxyalkyl groups having three to four carbon atoms.

2. Composition according to claim 1, wherein said 4-aminophenol derivative is selected from the group consisting of 4-amino-2-methoxymethylphenol, 4-amino-2-ethoxymethylphenol, 4-amino-2-propoxymethylphenol, 4-amino-2-isopropoxymethylphenol and 4-amino-2-(2'-hydroxyethoxymethyl)-phenol.

3. Composition according to claim 1, wherein said developer substance is present in an amount of from 0.01 to 3.0 percent.

4. Composition according to claim 3, wherein said developer substance is present in an amount of from 0.1 to 2.5 percent.

5. Composition according to claim 1, wherein said coupler substance is selected from the group consisting of 1-napthol, resorcinol, 4-chlororesorcinol, 4,6-dichlororesorcinol, 2-methylresorcinol, 2-amino-4-(2'-hydroxyethylamino)-anisole, 5-amino-2-methylphenol, 2,4-diaminphenoxyethanol, 4-amino-2-hydroxyphenoxyethanol, m-aminophenol, 3-amino-4-chloro-6-methylphenol, 3-amino-2-methylphenol, 4-hydroxy-1,2-methylenedioxybenzene, 4-(2'-hydroxyethylamino)-1,2-methylenedioxybenzene, 2,4-diamino-5-ethoxytoluene, 2,4-diaminobenzyl alcohol, m-phenylenediamine, 4-hydroxyindole, 3-amino-5-hydroxy-2,6-dimethoxypyridine and 3,5-diamino-2,6-dimethoxypyridine.

6. Composition according to claim 1, wherein said coupler substance is present in an amount of from 0.01 to 3.0 percent.

7. Composition according to claim 6, wherein said coupler substance is present in an amount of from 0.1 to 2.5 percent.

8. Composition according to claim 1, wherein the total amount of said coupler substance and said developer substance is from about 0.1 to 6.0 percent.

9. Composition according to claim 8, wherein the total amount of said coupler substance and said developer substance is from about 0.5 to 4.0 percent.

10. Composition according to claim 1, further comprising 6-amino-2-methyl phenol.

11. Composition according to claim 1, further comprising 2-amino-5-methyl phenol.

12. Composition according to claim 1, further comprising at least one directly applied hair dye selected from the group consisting of Diamond Fuchsin(C.I. 42 510), Leather Ruby HF (C.I. 42 520), 2-nitro-1,4-diaminobenzene, 2-amino-4-nitrophenol, 2-amino-5-nitrophenol, 2-amino-4,6-dinitrophenol, 2-amino-5-(2'-hydroxyethylamino)-nitrobenzene, 4-(2'-hydroxyethylamino)-3-nitrotoluene, 1-(2'-Ureidoethyl)-amino-4-nitrobenzene, Acid Brown 4 (C.I. 14 805), 1,4-diaminoanthraquinone and 1,4,5,8-tetraminoanthraquinone.

13. Composition according to claim 1, wherein said composition has a pH value of from 8.0 to 11.5.

14. Composition according to claim 1, wherein said 4-aminophenol derivative of the formula (I) is 4-amino-2-propoxymethylphenol.

15. Composition according to claim 1, wherein said 4-aminophenol derivative of the formula (I) is 4-amino-2-isopropoxymethylphenol.

16. Composition according to claim 1, wherein said 4-aminophenol derivative of the formula (I) is 4-amino-2-(2'-hydroxyethoxymethyl)-phenol.

* * * * *